United States Patent [19]

Mitchell

[11] Patent Number: 4,516,975
[45] Date of Patent: May 14, 1985

[54] FORMED AND WASHABLE DIAPER

[76] Inventor: Debra J. Mitchell, 110 Calvert Ct., Piedmont, Calif. 94611

[21] Appl. No.: 588,349

[22] Filed: Mar. 12, 1984

[51] Int. Cl.³ .............................................. A41B 13/02
[52] U.S. Cl. ................................................. 604/385 A
[58] Field of Search ............... 604/384, 385, 378, 394, 604/396

[56] References Cited

U.S. PATENT DOCUMENTS

| 2,505,891 | 5/1950 | Grogan et al. | 604/394 |
| 2,664,895 | 1/1954 | Shulman | 604/394 |
| 3,646,937 | 3/1972 | Gellert | 604/390 |
| 3,828,785 | 8/1974 | Gamm et al. | 604/394 |
| 3,848,594 | 11/1974 | Buell | 604/390 |
| 3,860,003 | 1/1975 | Buell | 604/385 |
| 4,041,951 | 8/1977 | Sanford | 604/375 |

Primary Examiner—John D. Yasko
Assistant Examiner—Christa K. Scott
Attorney, Agent, or Firm—Bruce & McCoy

[57] ABSTRACT

A formed and washable diaper comprised of multiple layers of material including an inner layer of soft non-irritating absorbent washable fabric, a middle layer of washable batting to form the frame of the diaper, an absorbent and moisture retentative mildew-resistant washable felt layer, and an outer moisture barrier layer of fabric, said diaper being formed with a configuration which is body-fitting and includes extra absorbency material disposed from front to rear of the wearer's body in the crotch area and which conforms thereto due to the unique method of construction of the diaper.

3 Claims, 7 Drawing Figures

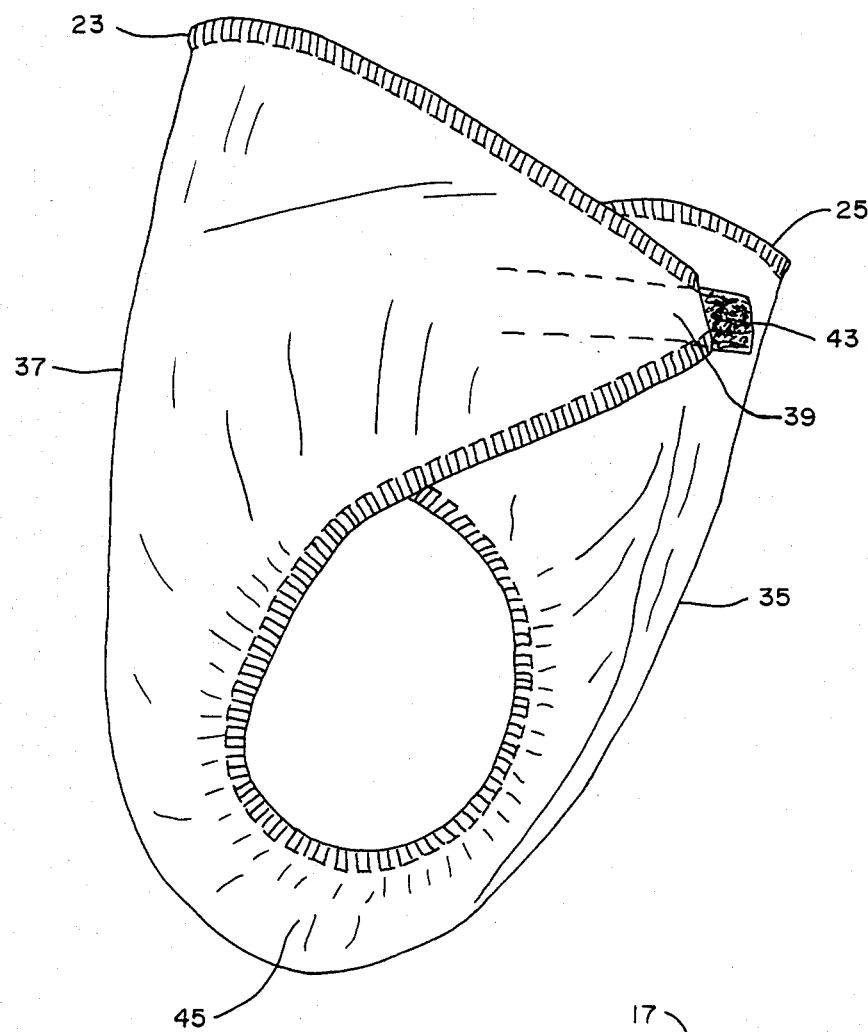
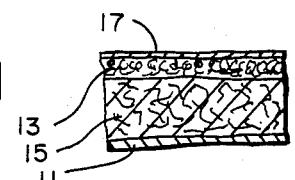
FIG.—1
FIG.—7
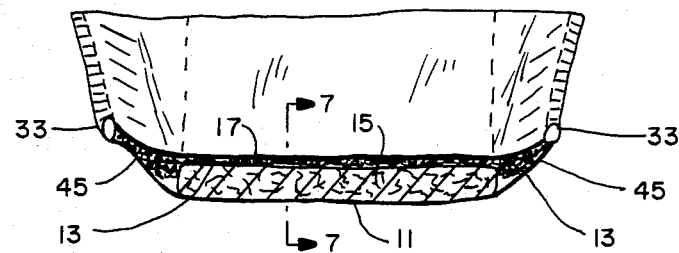
FIG.—6

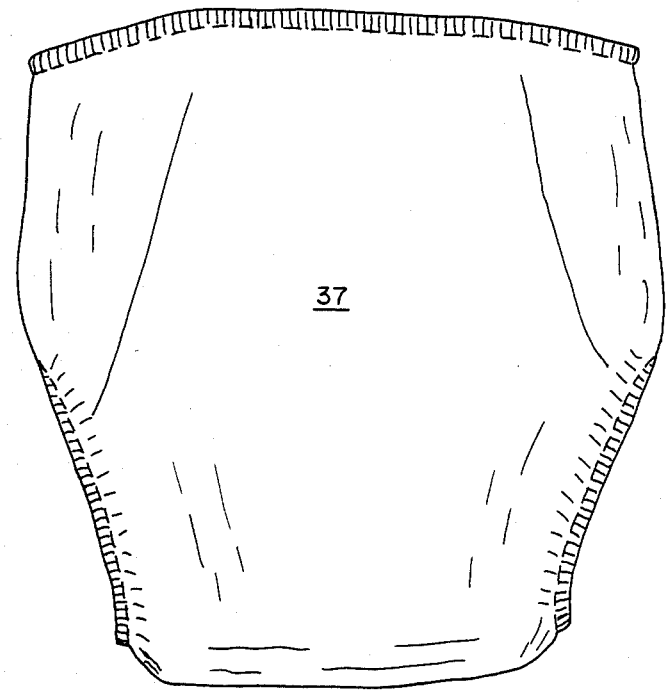
FIG.—2
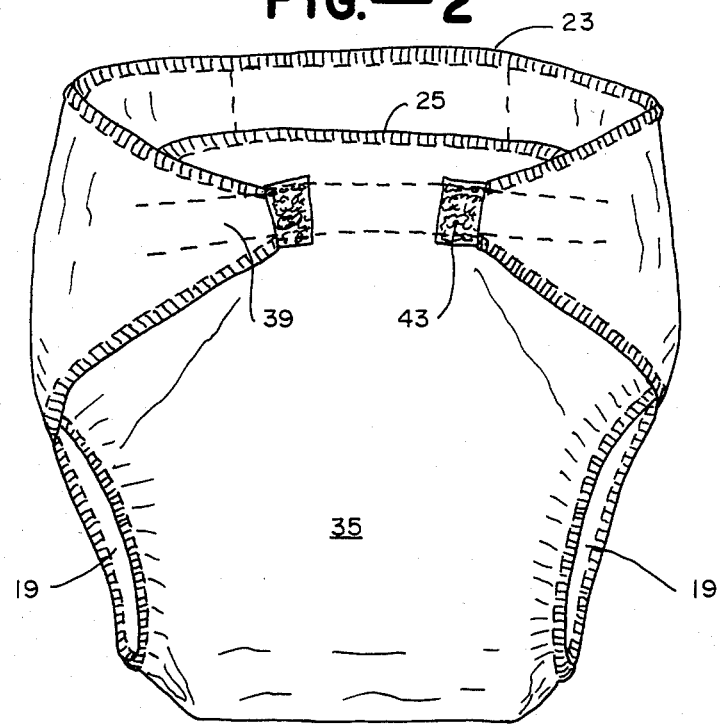
FIG.—3

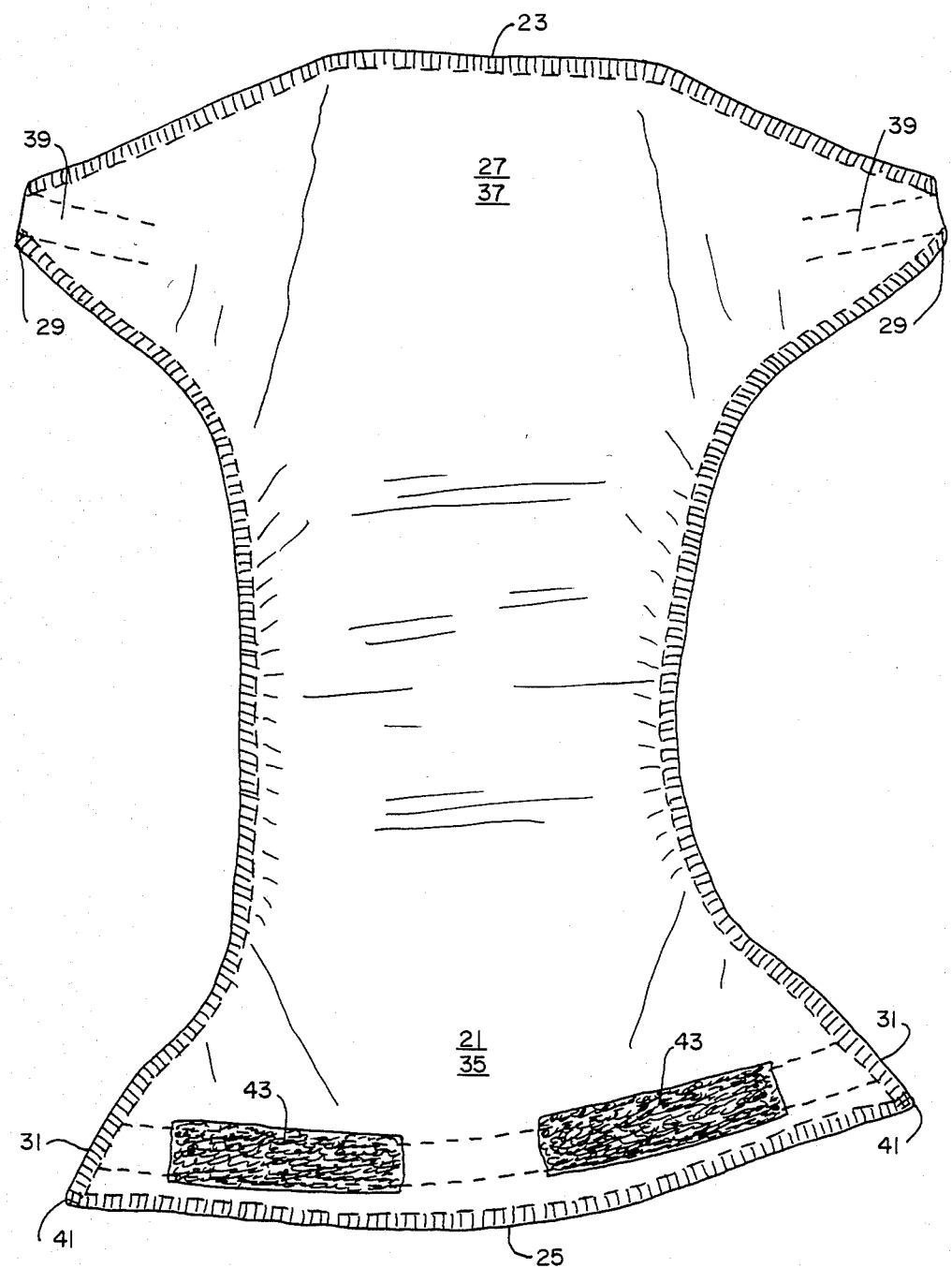
FIG. — 4

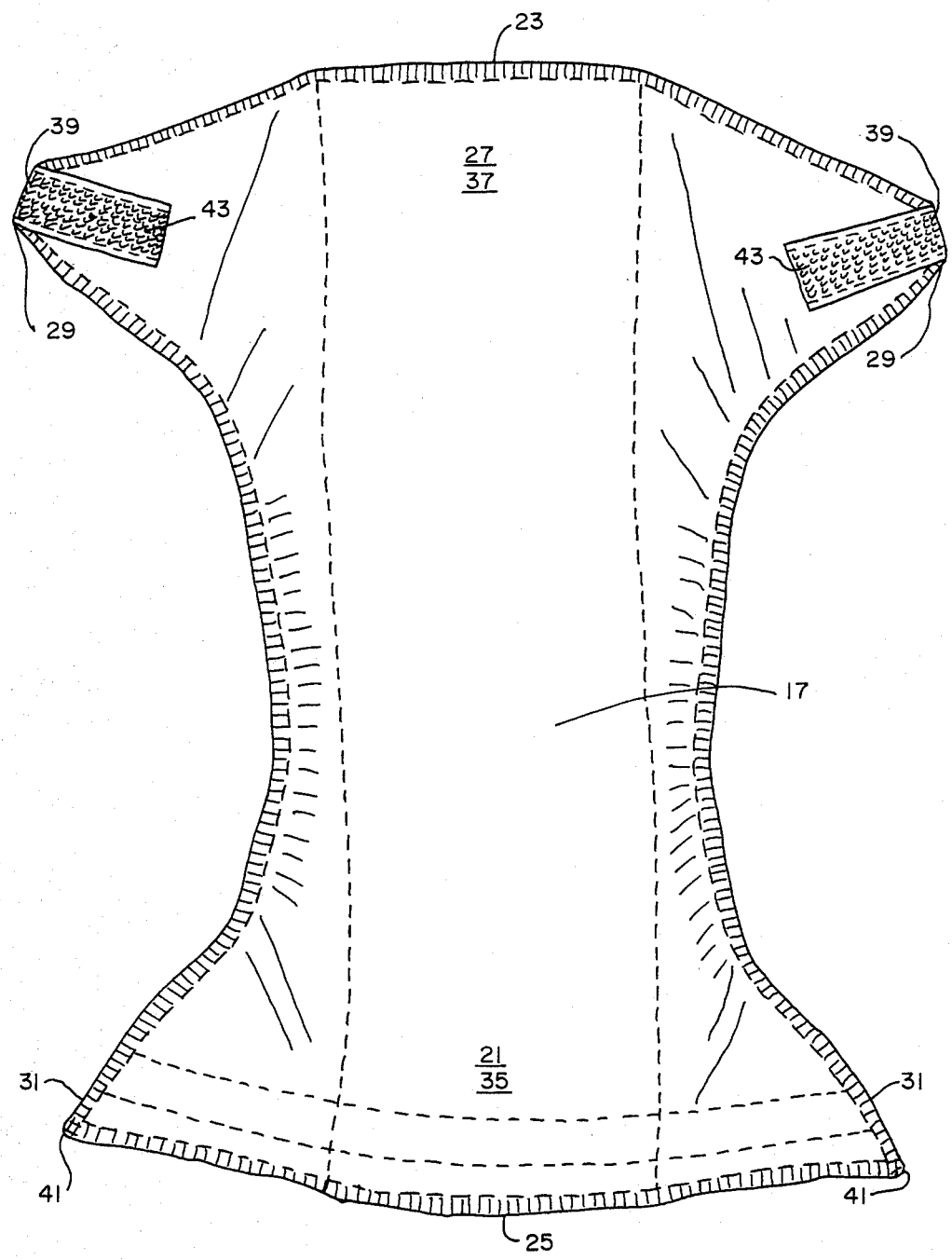
FIG.—5

FORMED AND WASHABLE DIAPER

CROSS-REFERENCES TO RELATED APPLICATIONS

The present invention is related to U.S. Patent Application Ser. No. 06/365,157 filed Apr. 5, 1982, for a Reusable Fluid Absorption Pad and assigned to Art Unit 336.

BACKGROUND OF THE INVENTION

1. Field of the Invention

The present invention relates to diapers and more particularly to a formed and washable diaper having multiple layers of different types of material for different functions which is reusable and conforms to the body of the wearer.

2. Description of the Prior Art

There are numerous multiple layer fabric diapers on the market such as those described in U.S. Pat. Nos.: 3,646,937; 3,848,594; 3,860,003; and 4,041,951. The problem with these diapers is that all of them are made of disposable materials which cannot be washed and reused because they cannot stand the stress of the washing procedure and the high temperatures of tumble drying which occur in clothes washing and drying machinery. Disposable diapers are very expensive when compared with reusable diapers which are more expensive but can be washed and reused many times.

There are other problems with disposable diapers. The chemicals utilized in the fragrances put into the diapers have proven to cause skin irritation and bronchial infection and irritation. Numerous cases of infant deaths have been reported which have been determined to have been due to inhalation of particles and pieces of disposable diapers which were apparently torn or picked off the diaper by the infants when the diapers became wet and lost their tensile strength. Additional deaths have been determined to have occurred from suffocation when the diapers became wet and the securement means tore off and the diaper ended up covering the infant's face. The present invention has been designed to at least minimize but in most cases eliminate these problems.

SUMMARY OF THE INVENTION

The present invention is a formed and washable diaper comprised of a multiplicity of layers of material including an outer layer forming a moisture barrier cover, a moisture absorbent felt layer, a middle layer of batting forming the frame of the diaper, and a soft inner facing layer made of a non-irritating absorbent washable fabric.

The diaper has a particular body enclosing configuration due to its unique construction which includes an hour-glass outline with each of the hour-glass shaped sides forming a continuous sculpted crescent shaped concave curve. The top and bottom edges are generally curved slightly convex upward and downward respectively. The upper end of the diaper is slightly longer in lateral length than the bottom end whereby when the diaper is placed on the wearer with the top end disposed at the back of the body and with the bottom end pulled up between the wearer's legs and disposed with the bottom end in front on the stomach of the wearer's body, the two edges of the top end of the diaper will wrap around the wearer's body from behind and overlap the two edges at the bottom end of the diaper disposed on the wearer's stomach.

The lateral curved vertically disposed edges of the diaper are provided with a stretched elastic edging which is secured to the material for a portion of the length of the curved edges whereby when the elastic is released, and allowed to retract, the diaper is pulled into a U-shaped configuration.

The outer edges, the inner, middle and outer layers of the material are formed co-extensive through the extent of the configuration of the diaper. The absorbent felt material, however, is disposed only in a strip from the top end down the diaper middle to the bottom and provides extra absorbency throughout the middle portion of the diaper.

The tabs formed by the top and bottom lateral edges or corners of the diaper are provided with adjustable strip and grip fasteners for securing the overlapping edges together to hold the diaper on the wearer's body.

OBJECTS OF THE INVENTION

It is therefore an important object of the present invention to provide a formed diaper which conforms to a wearer's body.

It is another object of the present invention to provide a washable diaper which can withstand both the stress of washing in automatic clothes washers and the high temperatures of hot air clothes dryers.

It is a further object of the present invention to provide a reusable diaper which provides an extra thick absorbent layer for retaining greater amounts of moisture than disposable diapers.

It is yet another object of the present invention to provide a diaper which is safe, non-irritating, mildewresistant, and does not require any pins to hold it on the wearer.

It is yet a further object of the present invention to provide a diaper which is adjustable in size and can be maintained in an inside out configuration for washing.

Other objects of the present invention will become apparent when the description of the preferred embodiment thereof is considered in conjunction with the accompanying drawings.

BRIEF DESCRIPTION OF THE DRAWINGS

FIG. 1 is a side elevation of the formed and washable diaper of the present invention;

FIG. 2 is a rear elevation of the diaper of the present invention;

FIG. 3 is a front elevation of the diaper of the present invention;

FIG. 4 is a bottom plan view of the diaper of the present invention in a stretched out configuration showing the outside thereof;

FIG. 5 is a top plan view of the diaper of the present invention showing the inner side thereof in a stretched out configuration;

FIG. 6 is a partial cross-section of the diaper of the present invention taken along lines 6—6 of FIG. 1; and FIG. 7 is a partial cross-section of the diaper of the present invention taken along lines 7—7 of FIG. 6.

DESCRIPTION OF THE PREFERRED EMBODIMENT

The preferred embodiment of the formed and washable diaper of the present invention has a natural body-enclosing configuration which is due to its unique form of construction. It is substantially form-fitting to a wearer's body. It's primary use is for infants, but with proper sizing it can be used equally well for any incontinent person and geriatric patients. The material utilized in the construction of the diaper of the present invention permits it to be reused through an average of between 30 to 50 and up to 85 washings.

The present invention includes a non-allergenic moisture barrier outer layer 11 which prevents excreted fluids retained by the absorbent layers from passing through the diaper covering to the garments or bedclothes of the wearer. In the preferred embodiment, the outer layer is made of urethane coated 100% nylon taffeta.

The absorbent layer 15 is constructed of felt made from a needle punched rayon and polyester blend. This layer is of uniform thickness but is considerably thicker than the inner and outer layers and is formed in the shape of a narrow rectangle which in operative position extends fore and aft between the wearer's legs and covers the wearer's crotch area.

The middle layer 13 is a mildew-resistant washable batting made of spun rayon and polyester. The material characteristics of the batting permit it to function as a frame for the diaper to hold its shape and maintain its formed configuration once the construction of the diaper has been completed. It supports the other materials which are attached to both sides of it.

The inner layer 17 of the diaper is a soft nonirritating absorbent washable fabric that is disposed next to the skin of the wearer to absorb the excreted fluids and permit them to wick through to the absorbent layer. In the preferred embodiment, it is comprised of 100% cotton, but it has been found that a blend of up to 50% polyester with the cotton will also work satisfactorily.

The diaper has a particular body enclosing configuration due to its construction. This is created by forming the diaper in an outline described as somewhat of an hourglass but with the pinched in sides acutally being formed by a continuous sculpted crescent shaped concave curve on each of the lateral edges 19. These edges are narrowed more towards the bottom end 21 of the diaper which end forms the front thereof. The top and bottom edges 23, 25, respectively, of the diaper are also generally curved slightly convex upward and downward respectively. In actual practice, the flat top and bottom edges are tapered slightly toward the center of the diaper to provide the convex configuration.

The upper end 27 of the diaper is slightly longer in lateral length than the bottom end, whereby, when the diaper is placed on the wearer with the top end disposed at the back of the body, and with the bottom end 21 pulled up between the wearer's legs and disposed at the front of the wearer's body on the stomach, the two lateral edges 29 or corners of the top end of the diaper will wrap around the wearer's body from behind and overlap the two lateral edges 31 or corners formed by the bottom end of the diaper when it is disposed on the wearer's stomach. This configuration reduces the bulk of material that must be disposed between the wearer's legs.

In addition to providing a configuration which allows uniformity of thickness be disposed on the wearer's body without the bunching up of material, the unique construction of the diaper also causes it to be formed into a body enclosing configuration. This is done by providing the curved lateral vertically disposed edges 19 of the diaper with a stretched elastic edging 33 which is secured to the material of the diaper with an overlock stitch for that portion of the length of the curved edges which is disposed around the wearer's legs. This elastic 33 is stretched during the sewing operation whereby when the elastic is released and allowed to retract to its normal state of rest, the diaper is pulled into a U-shaped configuration. The resulting opposed portions of the U-shaped configuration are the front and rear flaps 35, 37, respectively, of the diaper.

The outer edges of the inner, middle, and outer layers, 11, 13, and 17, respectively, of the material forming the diaper are co-extensive throughout the extent of the configuration of the diaper, but the absorbent layer 15 is coextensive with only a portion of the other layers. The absorbent material is disposed in a strip from the top of the diaper 23 to the bottom 25 down through the middle of the diaper. It actually forms an elongated rectangle extending from one end of the diaper to the other which in operative position is disposed in the crotch of the wearer and due to its narrow configuration allows a more natural positioning of the wearer's legs while the diaper is being worn. This layer provides extra absorbency throughout the middle portion of the diaper throughout its length.

The tabs 39, 41 that are formed by the top and bottom lateral edges or corners of the diaper, 19 and 21, respectively, are provided with strip and grip fasteners 43 for securing the overlapping edges together to hold the diaper on the wearer's body. In the preferred embodiment, Velcro brand of similar fasteners are used which when positioned as shown in the drawings provide an adjustable perfect body-fitting securement means which is on the front of the diaper so that the wearer can be laid on his or her back to fasten the diaper. The wearer's legs are lifted, the top or rear of the diaper is slid underneath, the wearer's legs are allowed to drop on both sides of the diaper, the front flap is pulled up, the two tabs from the rear flap wrap over and press on those that lie on the front, and the diaper is automatically secured to the wearer with no further effort and particularly without pins that could possibly be stuck into the wearer by accident.

These fasteners and their arrangement also have a unique benefit in that when one turns the diaper inside out, the same fasteners will hold the diaper in an inverted or reverse configuration so that it can be put through the washing machine inside out and will continuously present the inner surface of the diaper to the washing and drying mediums. To reduce handling for diaper service users, grip tabs can be sewn behind the strip tabs so they can be simply folded over or flat on the diaper and stuck to it so they do not flop free and grab onto other clothes. In this latter arrangement, the diaper is washed in an extended configuration.

The absorbent layer portion of the diaper is slightly narrower in width than the narrowest section of the diaper between the top and bottom ends so that the remaining edges of the diaper extending laterally of the pad in the narrowest section are pulled upward into the middle of the U-shaped diaper when the elastic is allowed to retract. These two edges then form somewhat vertical side-walls 45 in the bottom of the diaper to enhance the form fitting configuration and to retain any exudate produced by the diaper wearer.

The present invention is 10 to 15 times more expensive per unit than disposable diapers presently on the market, but since it can be reused between 30 to as many as 85 times it is in effect between $\frac{1}{3}$ and 2/17 as expensive as a disposable diaper in overall cost. The benefits of the comfort and safety of having a non-allergenic, pinless diaper, which always retains its tensile strength so it cannot fall or be picked apart when it becomes wet, are self-evident. These advantages are not obtainable from disposable diapers.

Thus, it will be seen from this description of the preferred embodiment of the present invention that the formed and washable diaper disclosed and described herein achieves the objects and advantages attributable thereto, and while the invention has been described in considerable detail, it is not to be limited to such details as set forth except as may be necessitated by the appended claims.

I claim:

1. A formed and washable diaper comprised of
   a multiplicity of layers of material including a non-allergenic outer layer forming a moisture barrier cover,
   a moisture retentive mildew resistant washable felt layer,
   a middle layer of batting forming the frame of the diaper, and
   an inner facing layer of soft non-irritating absorbent washable fabric, said diaper having a particular body enclosing configuration due to its construction which includes an hour-glass outline with each of the hour-glass shaped sides forming a continuous sculpted crescent shaped concave curve with the top and bottom edges of the diaper being generally curved slightly convex upward and downward respectively, the upper end of said diaper being slightly longer in lateral length than the bottom end whereby when the diaper is placed on the wearer with the top end disposed at the back of the wearer's body and with the bottom end pulled up between the wearer's legs and disposed on the front of the wearer's body on the stomach, the two lateral edges of the top end of the diaper will wrap around the wearer's body from behind and overlap the two lateral edges at the bottom end of the diaper disposed on the wearer's stomach, the laterally curved vertically disposed edges of the diaper being provided with an elastic edging which is secured to said material for a portion of the length of the curved edges which surround the wearer's leg when the diaper is disposed in operative position whereby when the elastic is released after being secured to the diaper in a stretched condition along the edge of said diaper and allowed to retract, said diaper is retracted into a U-shaped configuration with the resulting opposed portions being the front and rear flaps of said diaper, the outer edges of said inner, middle, and outer layers of said material being co-extensive throughout the extent of the configuration of the diaper, said absorbent felt layer being disposed in a narrow rectangular strip from the top to the bottom down the middle of said diaper to provide extra absorbency throughout the middle portion of said diaper, and
   tabs formed by the top and bottom lateral edges or corners of said diaper being provided with adjustable stick and grip fasteners for securing said overlapping lateral edges together to hold the diaper on the wearer's body.

2. The formed and washable diaper of claim 1 wherein said absorbent middle layer portion of said diaper is slightly narrower in width in the narrowest portion of said diaper between the top and bottom ends thereof so that the remaining edges of the diaper alongside the extra absorbent portion are pulled upward into the middle of the U-shaped diaper when the elastic is released forming parallel vertical side-walls in the bottom of the diaper.

3. The formed and washable diaper of claims 1 and 2 wherein said outer layer is made of urethane coated 100% nylon taffeta; said absorbent felt layer is made of needle punched rayon and polyester; said batting layer is made spun rayon and polyester; and inner layer is made of cotton or a cotton blend.

* * * * *